US 9,737,703 B2

(12) United States Patent
Carbunaru et al.

(10) Patent No.: US 9,737,703 B2
(45) Date of Patent: Aug. 22, 2017

(54) METHOD TO ENHANCE AFFERENT AND EFFERENT TRANSMISSION USING NOISE RESONANCE

(75) Inventors: Rafael Carbunaru, Valley Village, CA (US); Michael Moffitt, Valencia, CA (US); Kristen Jaax, Santa Clara, CA (US); Andrew DiGiore, Santa Monica, CA (US); Courtney Lane, Ventura, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 1308 days.

(21) Appl. No.: 12/501,170

(22) Filed: Jul. 10, 2009

(65) Prior Publication Data

US 2011/0009919 A1 Jan. 13, 2011

(51) Int. Cl.
*A61N 1/00* (2006.01)
*A61N 1/05* (2006.01)
*A61N 1/36* (2006.01)

(52) U.S. Cl.
CPC ....... *A61N 1/0551* (2013.01); *A61N 1/36057* (2013.01); *A61N 1/36071* (2013.01);
(Continued)

(58) Field of Classification Search
CPC ............... A61N 1/0551; A61N 1/0529; A61N 1/36057; A61N 1/36071; A61N 1/36114; A61N 1/36128; A61N 1/36164
(Continued)

(56) References Cited

U.S. PATENT DOCUMENTS 4,338,945 A * 7/1982 Kosugi et al. ................. 607/46
6,032,074 A 2/2000 Collins
(Continued)

FOREIGN PATENT DOCUMENTS

EP 1 608 303 6/2005
EP 1 909 894 4/2008
(Continued)

OTHER PUBLICATIONS

Rutkove, Seward B., M.D., Overview of upper extremity peripheral nerve syndromes, UpToDate.com, May 1, 2009 (14 pages).
(Continued)

*Primary Examiner* — Mallika D Fairchild
(74) *Attorney, Agent, or Firm* — Faegre Baker Daniels LLP (57) ABSTRACT

Methods of providing therapy to a patient are provided. In one method, the patient has a neuron to which a sub-threshold biological electrical stimulus is applied. The method comprises applying electrical noise energy to the neuron, wherein resonance between the biological electrical stimulus and the electrical noise energy is created, such that an action potential is propagated along the axon of the neuron. In another method, the patient has a neuron to which a supra-threshold biological electrical stimulus is applied. This method comprises applying supra-threshold electrical noise energy to the neuron, thereby preventing an action potential from being propagated along the axon of the neuron. Still another method comprises applying an electrical stimulus to a neuron, and applying supra-threshold electrical noise energy to the neuron, thereby preventing or reversing any neurological accommodation of the neuron that may occur in response to the electrical stimulus.

2 Claims, 10 Drawing Sheets

(52) U.S. Cl.
CPC ...... *A61N 1/36114* (2013.01); *A61N 1/36128* (2013.01); *A61N 1/36164* (2013.01); *A61N 1/0529* (2013.01)

(58) Field of Classification Search
USPC .................................. 607/45, 46, 55–57, 1, 2
See application file for complete search history.

(56) References Cited

U.S. PATENT DOCUMENTS

| | | | |
|---|---|---|---|
| 6,249,704 | B1* | 6/2001 | Maltan et al. ............... 607/57 |
| 6,516,227 | B1 | 2/2003 | Meadows et al. |
| 6,895,280 | B2 | 5/2005 | Meadows et al. |
| 7,010,351 | B2 | 3/2006 | Firlik et al. |
| 7,146,217 | B2* | 12/2006 | Firlik et al. ............... 607/45 |
| 7,539,538 | B2 | 5/2009 | Parramon et al. |
| 7,877,136 | B1* | 1/2011 | Moffitt et al. ............... 607/2 |
| 2003/0139781 | A1 | 7/2003 | Bradley et al. |
| 2004/0073271 | A1 | 4/2004 | Harry et al. |
| 2004/0173220 | A1 | 9/2004 | Harry et al. |
| 2005/0033377 | A1* | 2/2005 | Milojevic et al. ............... 607/45 |
| 2005/0267546 | A1 | 12/2005 | Parramon et al. |
| 2006/0015153 | A1* | 1/2006 | Gliner et al. ............... 607/45 |
| 2007/0025608 | A1 | 2/2007 | Armstrong |
| 2007/0027486 | A1 | 2/2007 | Armstrong |

FOREIGN PATENT DOCUMENTS

| | | |
|---|---|---|
| WO | WO 2004/080528 A1 | 9/2004 |
| WO | WO 2004/080528 A3 | 9/2004 |
| WO | WO 2007018793 A1 | 2/2007 |

OTHER PUBLICATIONS

Denac, Helena et al., Structure, function and pharmacology of voltage-gated sodium channels, Naunyn-Schmiedeberg's Arch Pharmacol (2000) 362: 453-479.
Rutkove, Seward B., M.D., Overview of lower extremity peripheral nerve syndromes, UpToDate.com, May 1, 2009 (19 pages).
Rutkove, Seward B., M.D., Overview of lower extremity peripheral nerve syndromes, UpToDate.com, May 1, 2009 (14 pages).
Weisstein, Eric W., Stochastic Resonance, from Mathworld—A Wolfram Web, Resource: http/mathworld.wolfram.com/StochasticResonance.html (1page).

* cited by examiner

METHOD TO ENHANCE AFFERENT AND EFFERENT TRANSMISSION USING NOISE RESONANCE

FIELD OF THE INVENTION

The present invention relates to tissue stimulation systems, and more particularly, to a system and method for conditioning and stimulating nerve tissue.

BACKGROUND OF THE INVENTION

There are many diseases, conditions, and syndromes where the propagation of electrical signals via neurological pathways may be hindered or inhibited, such as nerve entrapment syndromes, nerve compression nerve ischemia/infarct, radiation-induced injury, brain injury, brain diseases, brain disorders, inflammation, and degeneration.

Figure 1:
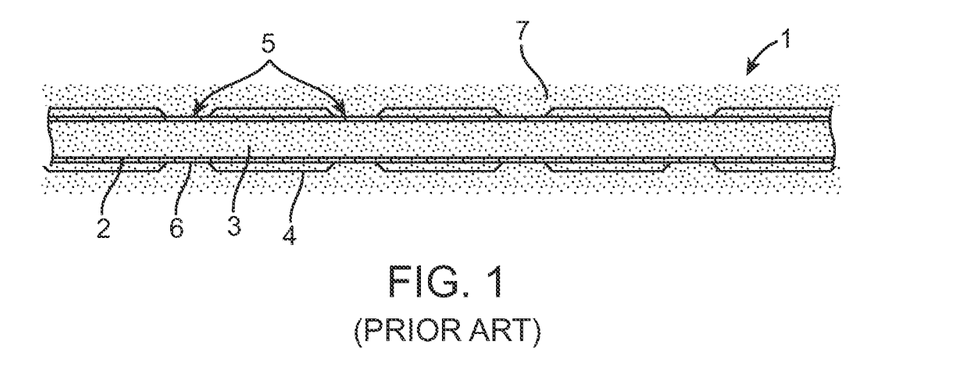
FIG. 1 is a cross-sectional view of a typical neuron.

To better understand the effect of diseases, conditions, and syndromes on neurological pathways, a basic understanding of the propagation of electrical signals within neural tissue will be helpful. Referring to FIG. 1, a typical neuron 1 that can be found in the white matter of the spinal cord or brain includes an axon 2 containing ionic fluid (and primarily potassium and sodium ions) 3, a myelin sheath 4, which is formed of a fatty tissue layer, coating the axon 2, and a series of regularly spaced gaps 5 (referred to as "Nodes of Ranvier"), which are typically about 1 micrometer in length and expose a membrane 6 of the axon 2 to extracellular ionic fluid 7. When an action potential (i.e., a sharp electrochemical response) is induced within the neuron 1, the transmembrane voltage potential (i.e., a voltage potential that exists across the membrane 6 of the axon 2) changes, thereby conducting a neural impulse along the axon neuron 1 as sodium and potassium ions flow in and out of the axon 2 via the membrane 6.

Figure 2:
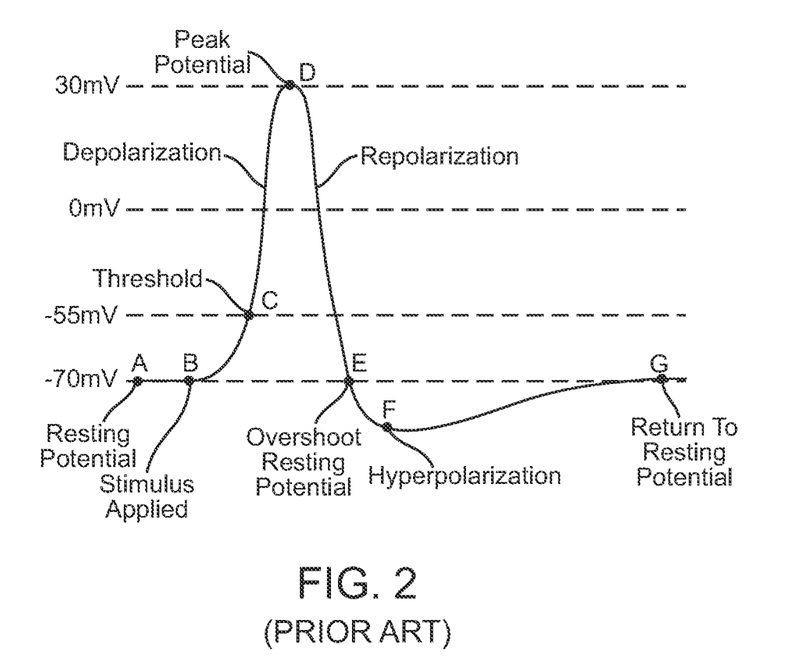
FIG. 2 is a diagram of the transmembrane voltage potential during an action potential evoked within the axon of the neuron of FIG. 1.

In particular, as shown in FIG. 2, when the axon 2 is at rest (point A), the interior of the axon 2 has a transmembrane voltage potential (i.e., the voltage potential of the interior relative to the exterior of the axon 2) of −70 to −80 mV. In response to a stimulation pulse (point B), which can be defined as an electrical signal that is large enough to evoke an action potential within the axon 2, the negative transmembrane voltage potential moves toward a more positive excitation threshold, thereby causing ionic current to inwardly flow into the axon 2, resulting in a change of the transmembrane voltage to a more positive value and approaching a threshold value (i.e., the transmembrane voltage potential at which an action potential is evoked, and in this case −55 mV) (point C). The transmembrane voltage potential then decreases rapidly, depolarizing axon 2 (high positive slope curve between point C and point D). Notably, the depolarization of the axon 2 is an all-or-nothing response (i.e., once the transmembrane voltage exceeds the threshold value, the action potential is propagated along the length of the axon 2). When the change in transmembrane voltage potential reaches a certain level (in this case 30 mV) (point D), ionic current outwardly flows out of the axon 2, resulting in a rapid change of the transmembrane voltage (becomes more negative), and repolarizing the axon 2 (negative slope curve between point D and point E). When the increase in transmembrane voltage potential reaches the resting voltage potential (point E), ionic current continues to outwardly flow out of the axon 2, thereby causing the negative change in the transmembrane electrical potential to continue beyond the resting electrical potential; that is, the axon 2 becomes hyperpolarized (point F). During this refractory period, the axon 2 returns to its resting period (point G) until another stimulation signal is applied to the axon 2.

Significantly, in myelinated axons, voltage-gated sodium channels (VGSCs), which are responsible for the initial inward current during the depolarization phase of an action potential (in excitable cells), are grouped in the nodes of Ranvier 5 (i.e., the areas between each myelinated section of the axon 2). Thus, because ion flow can only occur at the nodes 5 where the membrane 6 of the axon 2 is exposed to the extracellular ionic fluid 7, and due to the low capacitance of the myelinated sections of the axon 2, the neural impulse will actually jump along the axon 2 from one node 5 to the next node 5.

In this manner, the myelin sheath 4 serves to speed the neural impulse by insulating the electrical current and making it possible for the impulse to jump from node to node along the axon 2, which is faster and more energetically favorable than continuous conduction along the axon 2. Therefore, a small amount of charge (e.g., an action potential) may propagate a great distance along the axon 2.

Oftentimes, neurological conditions, syndromes, and diseases, such as multiple sclerosis and Guillain-Barre syndrome, cause demyelination of the axon 2, which can have devastating effects on behavior and neural function, because the lack of myelin slows down the conductions of, and may even block, action potentials that otherwise are conducted along axons within a nervous system. As an action potential moves from a myelinated region to a bare (demyelinated or damaged) stretch of axon, it encounters a relatively high capacitance and low transmembrane resistance. Therefore, the inward current of this area must flow for a longer time to supply enough charge to depolarize the next segment of the nerve in order to propagate the action potential. Because the body may not be able to produce the increased inward current necessary to propagate the action potential along the axon, neural signals are often slowed or blocked in demyelinated axons.

Furthermore, when damage to brain tissue occurs, a neuronal phenomenon referred to as "neuroplasticity" (variously referred to as "brain plasticity," "cortical plasticity," or "cortical remapping") changes the organization of the brain in response to experiences. In most cases, neuroplasticity, as a natural process to compensate for a damaged region of the brain, is desirable. However, in some cases, neuroplasticity may not be desirable.

For example, the process of regenerating a severed nerve may be a long process. As such, it is important to maintain functionality of that nerve, as well as the cerebral neurons associated with the functioning of that nerve. However, without intervention, other neurological functions may take over those associated with the regenerating nerve via neuroplasticity. As another example, when someone loses the ability to hear, it is very important to get a cochlear implant as soon as possible so that neuroplasticity within the auditory sectors of the brain does not "erase" his or her ability to hear.

In some cases, neural tissue may be electrically stimulated to treat patients. While generally effective, the neural tissue may eventually accommodate to the stimulation, which entails a diminished neural response over time when there exists continuous input (in this case, electrical stimulation) due to cellular and synaptic mechanisms, thereby rendering the therapy less effective. For the purposes of this specification, the term "accommodation" generally refers to any mechanism that diminishes neural response due to continuous input.

There, thus, remains a need for an improved method and system that restores the ability of neurons affected by the aforementioned diseased states to efficiently propagate action potentials, and/or that prevents the occurrence of neuroplasticity, and/or prevents or reverses neurological accommodation.

SUMMARY OF THE INVENTION

In accordance with a first aspect of the present inventions, a method of providing therapy to a patient is provided. The patient has a neuron to which a sub-threshold biological electrical stimulus is applied. The method comprises applying electrical noise energy to the neuron, wherein resonance between the sub-threshold electrical stimulus and the electrical noise energy is created, such that an action potential is conveyed along an axon of the neuron. In one method, the electrical noise energy is sub-threshold.

The neuron may, e.g., have a damaged myelin sheath that causes the biological electrical stimulus to be sub-threshold. The neuron may be a higher-order neuron (e.g., second order or third order) or a first-order neuron. The neuron may be associated with a damaged anatomical region of the patient (e.g., a limb), in which case, the method may further comprise exercising the anatomical region while applying the electrical noise energy to the neuron.

In one method, the propagation of the action potential along the axon of the neuron initiates or supplements neuroplasticity in the central nervous system of the patient. In another method, the neuron is damaged (e.g., severed), in which case, the propagation of the action potential along the axon of the neuron is afferent, such that it reduces neuroplasticity in the central nervous system.

In accordance with a second aspect of the present inventions, another method of providing therapy to a patient. The patient has a neuron to which a supra-threshold biological electrical stimulus is applied. The method comprises applying supra-threshold electrical noise energy to the neuron, thereby preventing an action potential from being propagated along an axon of the neuron that would otherwise occur in response to the supra-threshold electrical stimulus. In one method, the application of the electrical noise energy to the neuron reduces or prevents neuroplasticity in a portion of the brain associated with the neuron. In another method, the patient suffers from a neurological disorder (e.g., chemical addition and/or tremor), and the supra-threshold electrical stimulus is generated as a result of the neurological disorder.

In accordance with a third aspect of the present inventions, still another method of providing therapy to a patient is provided. The method comprises applying an electrical stimulus to a neuron, and applying supra-threshold electrical noise energy to the neuron, thereby preventing or reversing any neurological accommodation of the neuron that may occur in response to the electrical stimulus. In one method, the electrical stimulus and the electrical noise energy are applied to the neuron at different times.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 3:
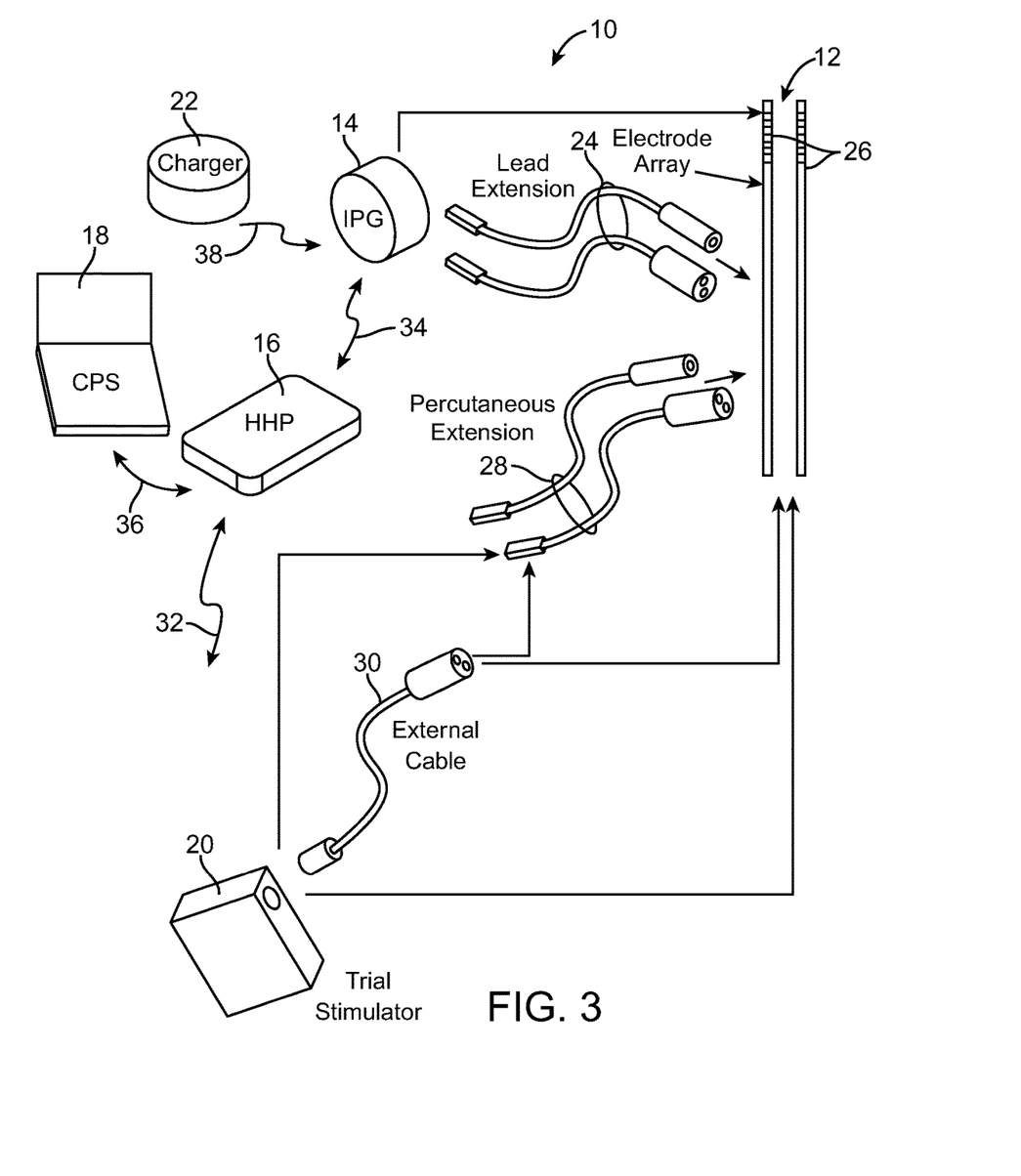
FIG. 3 is plan view of one embodiment of a spinal cord stimulation (SCS) system arranged in accordance with the present inventions.

Turning first to FIG. 3, an exemplary neuromodulation system 10 constructed in accordance with one embodiment of the present inventions generally includes one or more (in this case, two) implantable electrode leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more percutaneous lead extensions 24 to the electrode leads 12, which carry a plurality of electrodes 26 arranged in an array. In the illustrated embodiment, the electrode leads 12 are percutaneous leads, and to this end, the electrodes 26 are arranged in-line along the electrode leads 12. In alternative embodiments, the electrodes 26 may be arranged in a two-dimensional pattern on a single paddle lead. As will be described in further detail below, the IPG 14 includes pulse generation circuitry that delivers electrical noise energy in the form of a pulsed electrical waveform (i.e., a temporal series of electrical pulses or a continuous random process) to the electrode array 26 in accordance with a set of electrical parameters.

The ETS 20 may also be physically connected via the percutaneous lead extensions 28 and external cable 30 to the electrode leads 12. The ETS 20, which has similar pulse generation circuitry as that of the IPG 14, also delivers electrical noise energy to the electrode array 26 in accordance with a set of electrical parameters. The major difference between the ETS 20 and the IPG 14 is that the ETS 20 is a non-implantable device that is used on a trial basis after the electrode leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and electrode leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed electrical parameters to actively control the characteristics of the electrical noise energy output by the IPG 14.

The CP 18 provides clinician detailed electrical parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed electrical parameters provided by the CP 18 are also used to program the RC 16, so that the electrical parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 4:
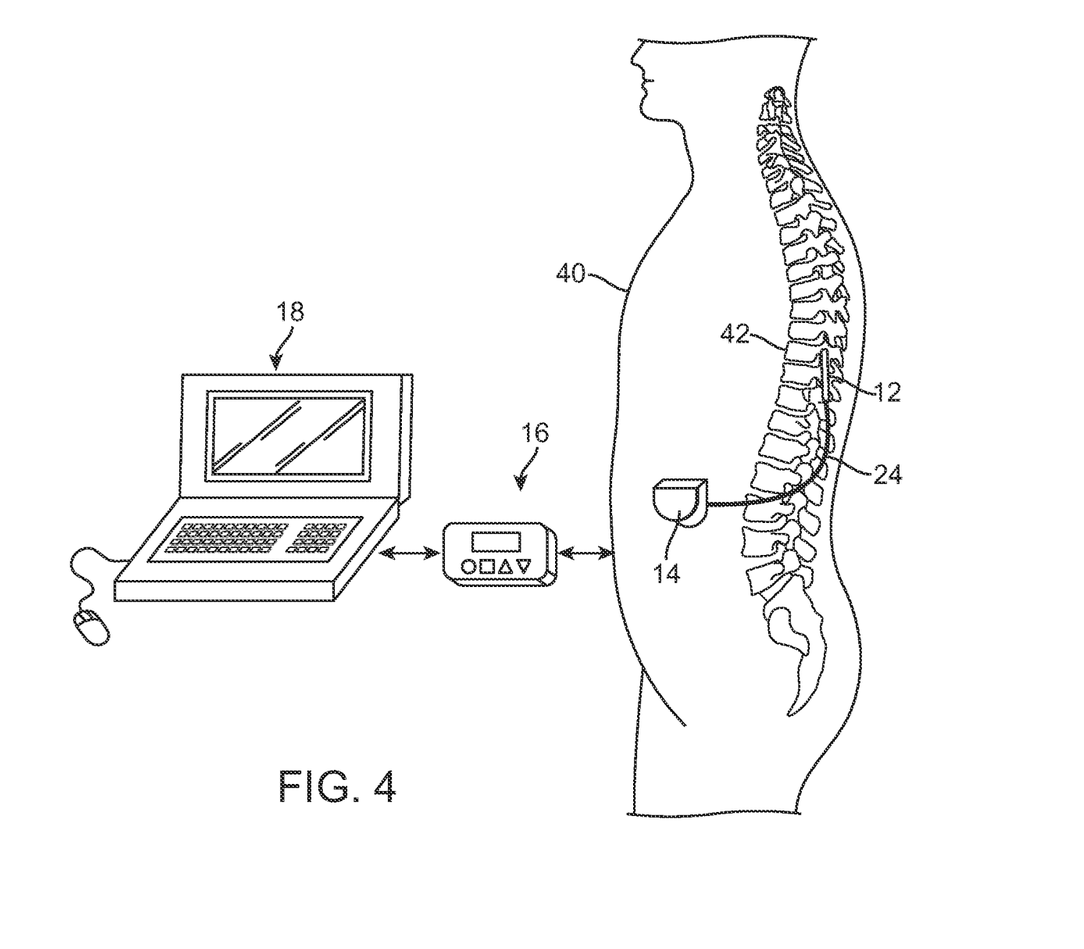
FIG. 4 is a plan view of the SCS system of FIG. 1 in use with a patient.

In one embodiment, the electrode leads 12 can be implanted within the spinal column 42 of a patient 40, as shown in FIG. 4. The preferred placement of the electrode leads 12 is adjacent, i.e., resting upon near, or upon the dura, adjacent to the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16. While the electrode leads 12 are illustrated as being implanted near the spinal cord area of a patient, the electrodes leads 12 may be implanted anywhere in the patient's body, including a peripheral region, such as a limb, or the brain and may stimulate neural elements, such as brain tissue, peripheral nerves, or sensor organs, etc.

Figure 5:
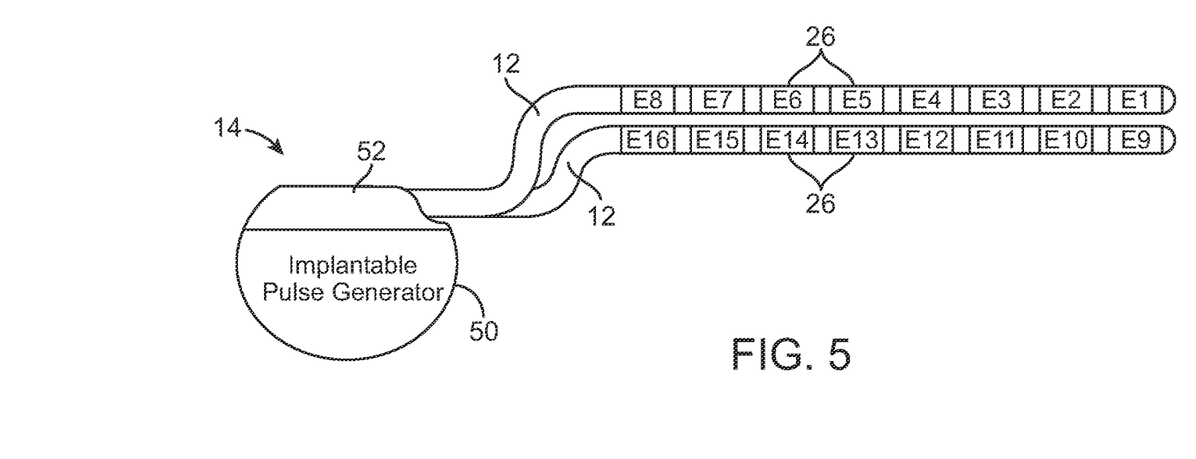
FIG. 5 is a plan view of an implantable pulse generator (IPG) and one embodiment of a stimulation lead used in the SCS system of FIG. 1.

Referring now to FIG. 5, the external features of the electrode leads 12 and the IPG 14 will be briefly described. One of the electrode leads 12 has eight electrodes 26 (labeled E1-E8), and the other electrode lead 12 has eight electrodes 26 (labeled E9-E16). The actual number and shape of leads and electrodes will, of course, vary according to the intended application. The IPG 14 comprises an outer case 50 for housing the electronic and other components (described in further detail below), and a connector 52 to which the proximal ends of the electrode leads 12 mate in a manner that electrically couples the electrodes 26 to the internal electronics (described in further detail below) within the outer case 50. The outer case 50 is composed of an electrically conductive, biocompatible material, such as titanium, and forms a hermetically sealed compartment wherein the internal electronics are protected from the body tissue and fluids. In some cases, the outer case 50 may serve as an electrode.

As briefly discussed above, the IPG 14 includes battery and pulse generation circuitry that delivers the electrical noise energy in the form of a pulsed electrical waveform to the electrode array 26 in accordance with a set of electrical parameters programmed into the IPG 14. Such electrical parameters may comprise electrode combinations, which define the electrodes that are activated as anodes (positive), cathodes (negative), and turned off (zero), percentage of electrical energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second), pulse shape, and burst rate (measured as the stimulation on duration per unit time).

The conveyance of the electrical energy will occur between two (or more) activated electrodes, one of which may be the IPG case 50. Electrical energy may be transmitted to the tissue in a monopolar or multipolar (e.g., bipolar, tripolar, etc.) fashion. Monopolar conveyance occurs when a selected one of the lead electrodes 26 is activated along with the case 50 of the IPG 14, so that electrical energy is transmitted between the selected electrode 26 and case 50. Bipolar conveyance occurs when two of the lead electrodes 26 are activated as anode and cathode, so that electrical energy is transmitted between the selected electrodes 26. For example, electrode E3 on the first lead 12 may be activated as an anode at the same time that electrode E11 on the second lead 12 is activated as a cathode. Tripolar conveyance occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

Figure 6A:
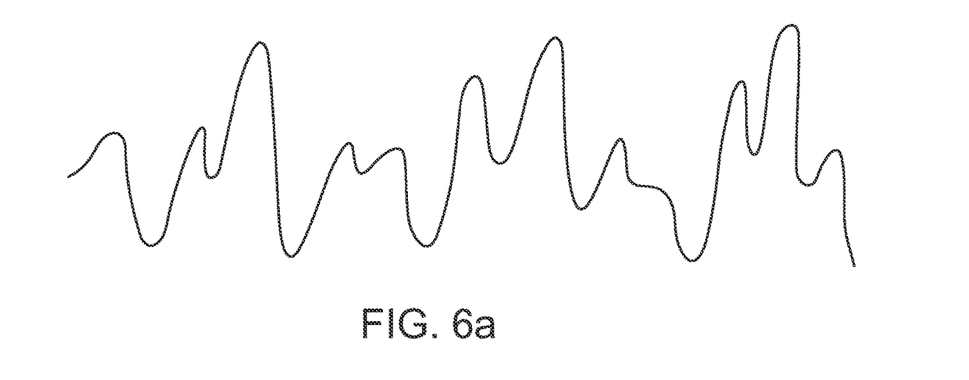
FIG. 6a is a diagram of continuous electrical noise energy generated in accordance with a Gaussian random process.
Figure 6B:
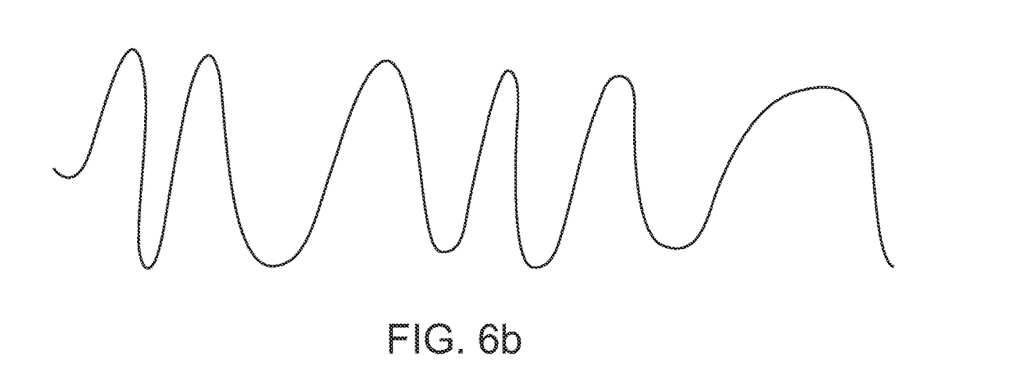
FIG. 6b is a diagram of sinusoidal electrical noise energy having a randomly varying phase.
Figure 6C:
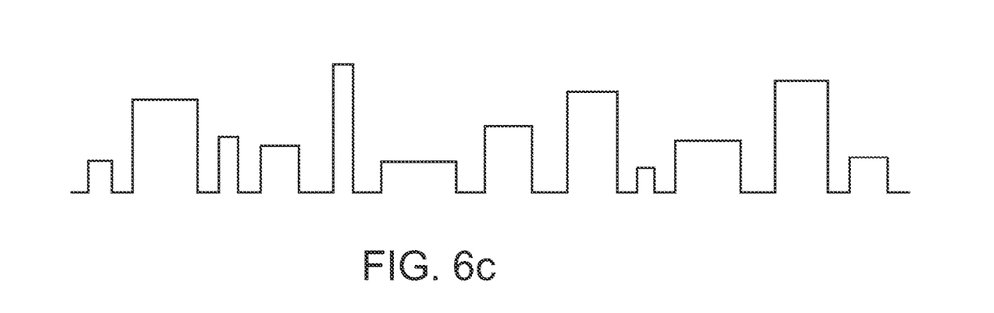
FIG. 6c is a diagram of an electrical noise energy pulse train having a randomly varying pulse amplitude, pulse width, and pulse rate.
Figure 7A:
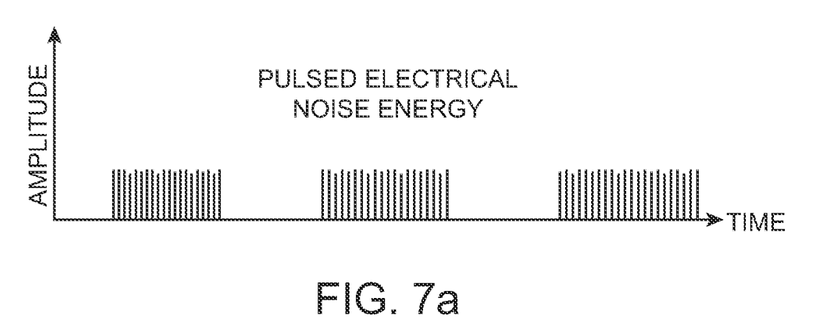
FIG. 7a is a diagram of pulsed electrical noise energy generated by the IPG of FIG. 5.
Figure 7B:
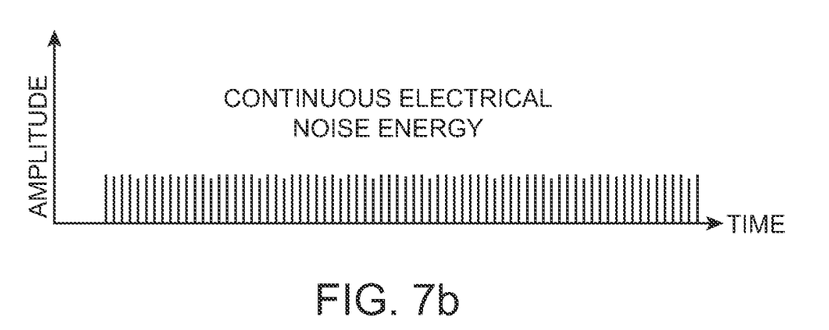
FIG. 7b is a diagram of continuous electrical noise energy generated by the IPG of FIG. 5.

Significantly, the IPG 14 also comprises circuitry configured for generating electrical noise energy. The electrical noise energy may be generated in accordance with a stochastic process. Notably, a stochastic process, which is the counterpart to a deterministic process, is a process where there is some indeterminacy in its future evolution described by probability distributions. This means that even if the initial condition (or starting point) is known, there are many possibilities the process might yield. For example, the electrical noise energy may be generated pseudo-randomly (i.e., a process that appears random, but is not, and appears to exhibit statistical randomness while being generated by an entirely deterministic causal process) or random. Types of random processes may include, e.g., a Gaussian random process that is a continuous signal, as shown in FIG. 6a, a sinusoid with randomly varying phase, as shown in FIG. 6b, or a pulse train with amplitude, pulse width, rate, or any combination of these, varying according to some distribution, as shown in FIG. 6c. As shown in FIG. 7a, the electrical noise energy may be pulsed on and off by the IPG 14. Alternatively, as shown in FIG. 7b, the electrical noise energy can be continuously conveyed by the IPG 14.

In the case, where the electrical noise energy has a randomly varying frequency, the frequency spectrum of such electrical noise energy may be, e.g., in the range of 100 Hz-20 KHz, preferably in the range of 200 Hz-5 KHz. Preferably, the center of the frequency spectrum of the electrical noise energy is greater than the pulse rate of the electrical noise energy. For example, the center frequency of the electrical noise energy may be five times greater than the pulse rate of the electrical noise energy. In one example, the frequency of a pulse train may vary randomly around 100 Hz. In a scenario where there is no variation in frequency, the period of the pulses would be 10 ms. In the scenario where there is a random variation in frequency (within limits), however, the time between adjacent pulses may be 10 ms±4 ms. So, a second pulse may be 7 ms from the first pulse, a third pulse may be 11 ms from the second pulse, a fourth pulse may be 10 ms from the third pulse, the fifth pulse may be a 6 ms from the fourth pulse, the sixth pulse may be 9 ms from the fifth pulse, and so on.

Figure 8:
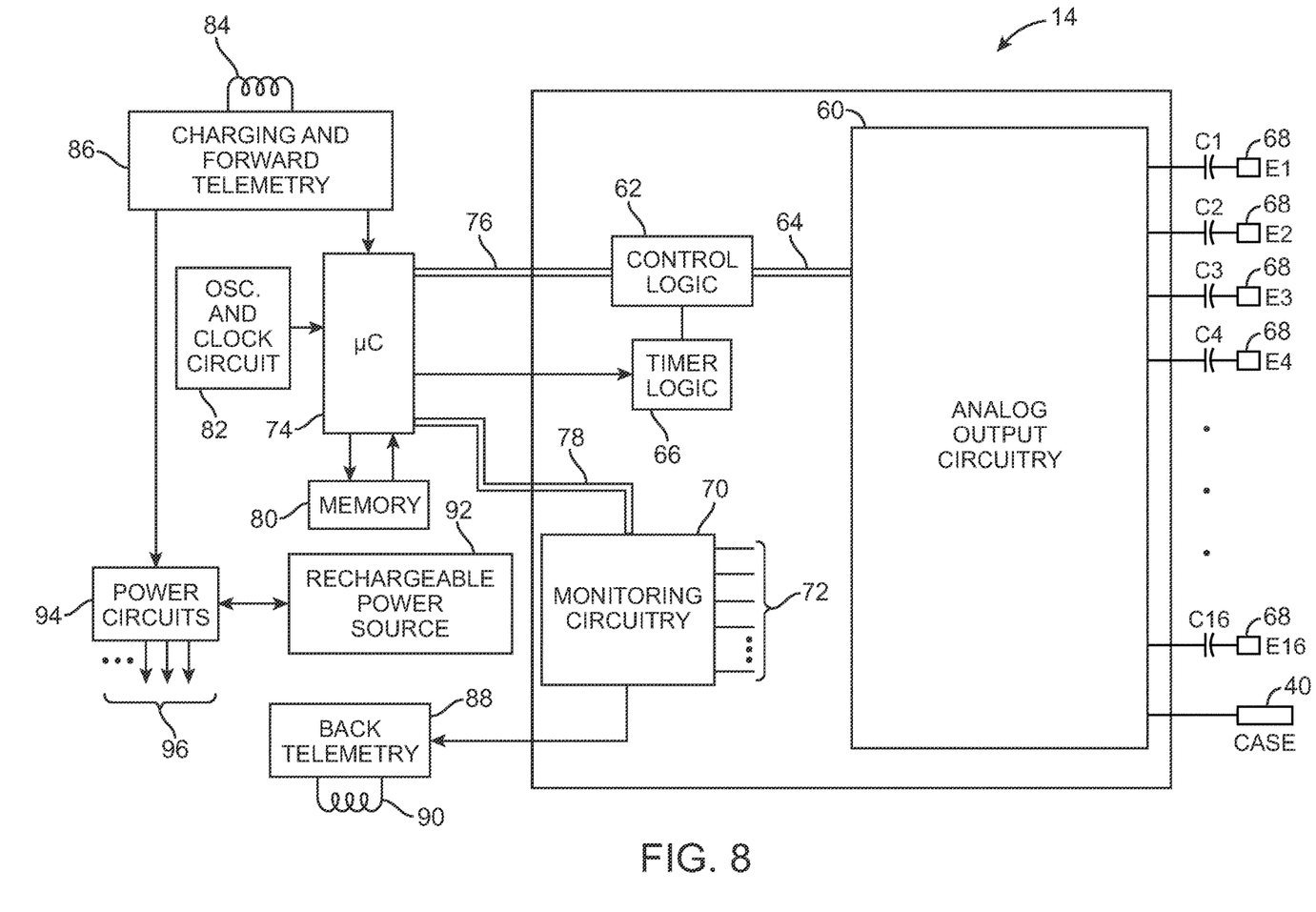
FIG. 8 is a block diagram of the internal components of the IPG of FIG. 5.

Turning next to FIG. 8, the main internal components of the IPG 14 will now be described. The IPG 14 includes electrical noise generation circuitry 60 configured for generating electrical noise energy. In this embodiment, the electrical noise energy is generated under control of control logic 62 over data bus 64. The electrical noise energy can be generated using band-pass filtered white noise. For the purposes of this specification, "white noise" is a randomized signal with a substantially flat power spectral density. That is, the signal contains substantially equal power within a fixed bandwidth at any center frequency. Alternatively, the electrical noise energy can be generated using band-pass filtered colored noise. For the purposes of this specification, "colored noise" is a randomized signal having a power spectral density that varies in accordance with some defined function. The center frequency and bandwidth of the filter will determine the degree of randomness in the signal. The randomness of the white noise (or colored noise) can be applied to electrical parameters; that is, electrode combinations (fractionalized or otherwise) or pulse parameters, such as the stimulation amplitude, interpulse interval, individual pulse shape and pulse width of an electrical pulsed waveform, to generate the electrical noise energy. Control of the pulse rate and pulse width of the electrical pulsed waveform is facilitated by timer logic circuitry 66, which may have a suitable resolution, e.g., 10 µs. The electrical noise energy generated by the electrical noise generation circuitry 60 is output via capacitors C1-C16 to electrical terminals 68 corresponding to the electrodes 26.

Figure 9:
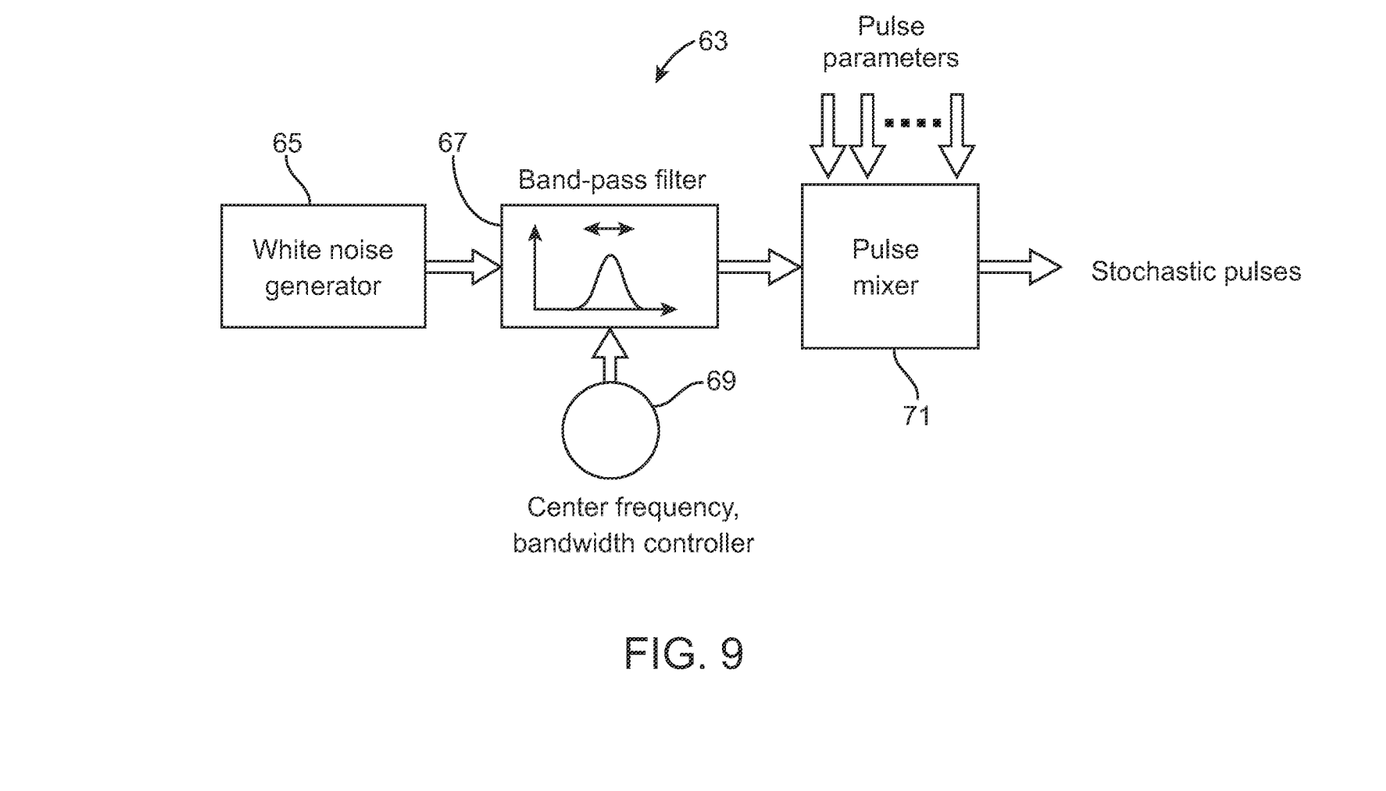
FIG. 9 is a block diagram of noise generation circuitry used in the IPG of FIG. 8.

The electrical noise generation circuitry 60 may be coupled between a fixed number of terminals 68, one of which may be the case, or may be selectively coupled between any number of terminals 68, e.g., via a switch (not shown). Referring to FIG. 9, one embodiment of the noise generation circuitry 60 comprises a white noise generator 65 configured for generating white noise used to generate the electrical noise energy. The noise generation circuitry 60 further comprises a bandpass filter 67 configured for filtering the white noise output by the white noise generator 65. The bandpass filter 67 includes a tuner 69 configured for adjusting the center frequency and bandwidth of the bandpass. In this manner, the tuner 69 can be used (e.g., by transmitting a control signal from an external control device, such as the RC 16 or IPG 18) to tune the electrical noise energy to provide the optimal therapy for the patient.

The noise generation circuitry 63 further comprises a pulse mixer 71 configured for stochastically varying one or more pulse parameters (e.g., pulse rate, pulse amplitude, and/or pulse duration) or electrode combinations based on the filtered white noise output by the bandpass filter 67, and generating and outputting the pulsed background pulses in accordance with the varied pulse parameter(s) or electrode combinations. Alternatively, instead of directly generating the electrical noise energy, circuitry can be used to stochastically vary the parameter(s) based on the filtered white noise. These stochastic parameter(s) can then be used by the microcontroller (described below). Alternatively, the noise generation circuitry 63 does not use a bandpass filter and pulse mixer, in which case, the noise generation circuitry 63 may directly output the filtered white noise to the electrodes, in which case, it may not have to be a pulse train.

Referring back to FIG. 8, the IPG 14 further comprises monitoring circuitry 70 for monitoring the status of various nodes or other points 72 throughout the IPG 14, e.g., power supply voltages, temperature, battery voltage, and the like. The monitoring circuitry 70 is also configured for measuring electrical parameter data (e.g., electrode impedance and/or electrode field potential). The IPG 14 further comprises processing circuitry in the form of a microcontroller (µC) 74 that controls the control logic 62 over data bus 76, and obtains status data from the monitoring circuitry 70 via data bus 78. The IPG 14 further comprises memory 80 and oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and electrical parameters (and if generated, the parameters output by the noise generation circuitry 61) stored in the memory 80. In controlling the operation of the IPG 14, the microcontroller 74 is able to generate electrical noise energy at the electrical terminals 68 using the noise generation circuitry 60, in combination with the control logic 62 and timer logic circuitry 66, thereby allowing each electrical terminal 68 (and thus, each electrode 26) to be paired or grouped with other electrical terminals 68 (and thus, other electrodes 26), including the monopolar case electrode, to control the polarity, amplitude, rate, pulse width, pulse shape, burst rate, and channel through which the electrical noise energy is provided. The microcontroller 74 facilitates the storage of electrical parameter data measured by the monitoring circuitry 70 within memory 80.

The IPG 14 further comprises a receiving coil 84 for receiving programming data (e.g., the operating program and/or electrical parameters) from the external programmer (i.e., the RC 16 or CP 18) in an appropriate modulated carrier signal, and charging, and circuitry 86 for demodulating the carrier signal it receives through the receiving coil 84 to recover the programming data, which programming data is then stored within the memory 80, or within other memory elements (not shown) distributed throughout the IPG 14.

The IPG 14 further comprises back telemetry circuitry 88 and a transmission coil 90 for sending informational data to the external programmer. The back telemetry features of the IPG 14 also allow its status to be checked. For example, when the CP 18 initiates a programming session with the IPG 14, the capacity of the battery is telemetered, so that the CP 18 can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the IPG 14 may be uploaded to the CP 18.

The IPG 14 further comprises a rechargeable power source 92 and power circuits 94 for providing the operating power to the IPG 14. The rechargeable power source 92 may, e.g., comprise a lithium-ion or lithium-ion polymer battery or other form of rechargeable power. The rechargeable source 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the receiving coil 84.

To recharge the power source 92, the external charger 22 (shown in FIG. 1), which generates the AC magnetic field, is placed against, or otherwise adjacent, to the patient's skin over the implanted IPG 14. The AC magnetic field emitted by the external charger induces AC currents in the receiving coil 84. The charging and forward telemetry circuitry 86 rectifies the AC current to produce DC current, which is used to charge the power source 92. While the receiving coil 84 is described as being used for both wirelessly receiving communications (e.g., programming and control data) and charging energy from the external device, it should be appreciated that the receiving coil 84 can be arranged as a dedicated charging coil, while another coil, such as the coil 90, can be used for bidirectional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference.

It should be noted that rather than an IPG, the neuromodulation system 10 may alternatively utilize an implantable receiver (not shown) connected to the electrode leads 12. In this case, the power source, e.g., a battery, for powering the implanted receiver, as well as control circuitry to command the receiver, will be contained in an external controller inductively coupled to the receiver via an electromagnetic link. Data/power signals are transcutaneously coupled from a cable-connected transmission coil placed over the implanted receiver. The implanted receiver receives the signal and generates the electrical noise energy in accordance with the control signals.

Having described the structure and functionality of the neuromodulation system 10, several methods of using the system 10 to provide therapy to a patient will now be described.

In one method, the neurostimulation system 10 may generate and apply electrical noise energy to a neural axon to which a biological electrical stimulus (i.e., an electrical stimulus that is naturally generated within the patient's body for the purpose of evoking an action potential within one or more neurons) is applied. The biological electrical stimulus may be generated in response to a command sent by the brain along an efferent nerve (such as a motor neuron that synapses to a muscle or an effector nerve that synapses to an organ), or may be generated in response to a sensory input sent along an afferent nerve (such as a sensory neuron), which may involve the special senses (e.g., vision, hearing, taste, and smell) or somatic senses (e.g., touch, pressure, position sense, pain, and thermal sensations of hot and cold).

If the neural axon is a sensory neuron, it may be a first order sensory neuron or a higher order (e.g., second or third order) sensory neuron. The cell bodies of first order sensory neurons are located in the dorsal root ganglia of spinal nerves or the ganglia of certain cranial nerves. The distal end of a first order sensor nerve fiber either acts as a sensor receptor located in the skin, subcutaneous tissue, muscles, and the various joint surfaces of the body (e.g., mechanoreceptors that sense body movement and pressure, or nocireptor fibers that sense tissue issue) or may be activated by some specialized type of sensor receptor (e.g., a Paccinian corpuscle in the dermis or a hair cell in the cochlea).

Integration of the sensory inputs occurs in the spinal cord to trigger the familiar spinal reflexes or may occur in the lower brain level. Some sensory input is carried by pathways to the higher brain, i.e., the cerebral cortex, which registers as consciousness or awareness of the sensation. To this end, the second order sensory neurons synapse with first order sensory neurons in the spinal cord or brainstem. The second order sensory neurons extend to a number of specific nuclei in the thalamus. The third order sensory neurons project from various specific thalamic nuclei to the appropriate region of the sensory cortex. Almost all sensory input passes through the thalamus on the way to the sensory cortex, with the exception being the olfactory pathway.

Under normal circumstances, whether the neuron is efferent or afferent, the biological electrical stimulus will evoke an action potential that is propagated along the length of the neural axon. However, in the exemplary case, the neural axon has been demyelinated due to, e.g., disease. As a result, the biological electrical stimulus, by itself, is sub-threshold in that its magnitude is not large enough to evoke the propagation of an action potential along the neural axon.

However, the resonance between the electrical noise energy and the sub-threshold electrical stimulus is created, such that an action potential is propagated along the neural axon. Notably, resonance occurs when noise that is added to system improves the performance of the system in some fashion. In particular, resonance occurs if the signal-to-noise ratio of a non-linear system or device increases for moderate values of noise intensity. In systems that require a threshold to be crossed, such as a neural system that requires the voltage threshold of the neural axon to be exceeded in order to evoke an action potential, the performance is improved by adding the magnitude of the electrical noise energy to the magnitude of the otherwise sub-threshold input stimulus to create a supra-threshold signal that evokes the action potential.

Figure 10:
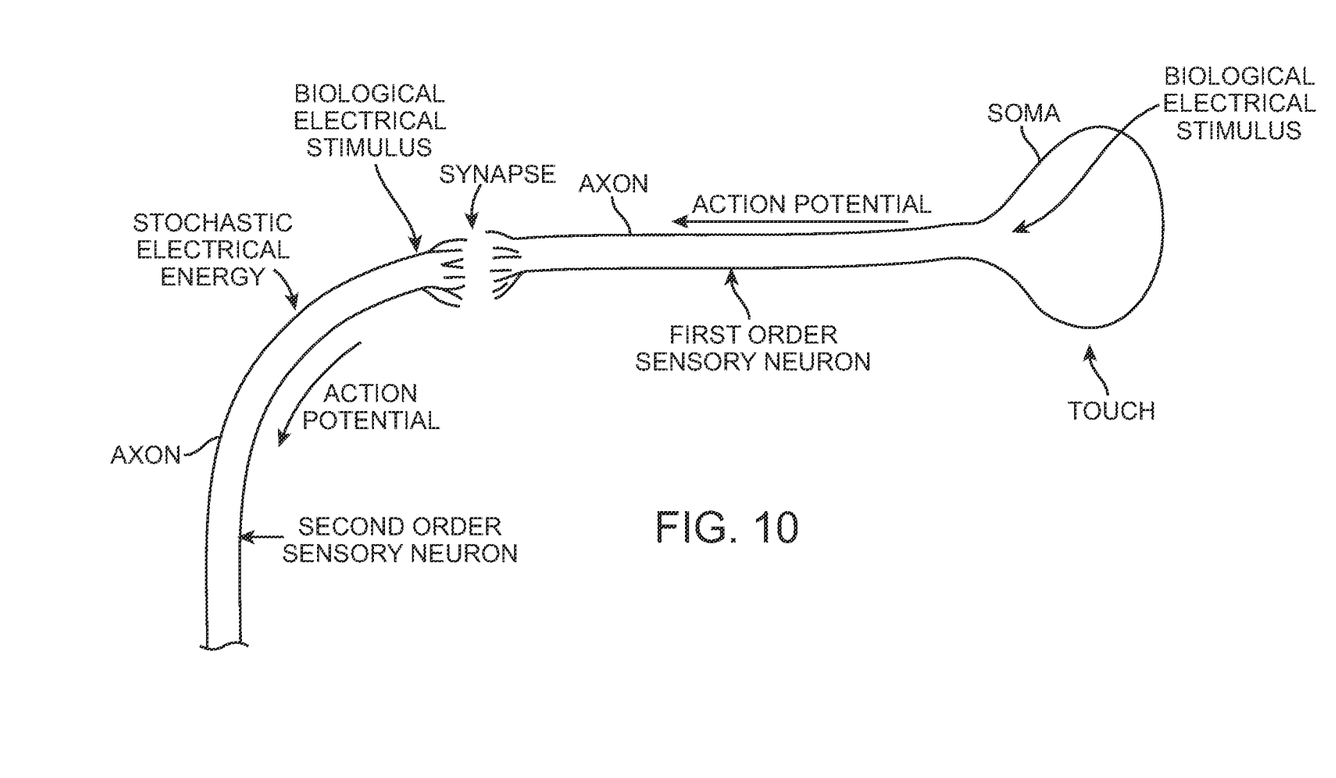
FIG. 10 is a plan view illustrating one method of providing therapy by the neuromodulation system of FIG. 3 to a second order sensory neuron to allow an action potential propagate in response to a biological trigger.

In one example illustrated in FIG. 10, a biological electrical stimulus is generated in the soma of a first order sensory neuron in response to a touch. Without any additional stimulus, an action potential propagated along the axon of the first order sensory neuron. The signal carried by the action potential is transmitted across the synapse to the second order neuron (in this case, a spinal cord fiber) where another biological electrical stimulus is generated. In this case, however, the spinal cord fiber has been demyelinated, and thus, an action potential is not generated in the spinal cord fiber absent the existence of an external electrical stimulus. The generation of the electrical noise energy via the neuromodulation system 10, however, will combine with the biological electrical stimulus generated in the second order neuron in an additive fashion to create a supra-threshold signal that will evoke the action potential for subsequent propagation along the axon of the second order neuron.

Notably, for lower noise intensities, a resulting supra-threshold signal is not created, so that an action potential will not be evoked, and for higher noise intensities, the neural axon will be dominated by the noise. Thus, the application of electrical noise energy of a moderate magnitude to the neural axon is desired in order to evoke the action potential without overloading the neural axon. For example, with reference to FIG. 11, a resulting signal created by the addition of relatively low level electrical noise energy to a biological electrical stimulus may not be great enough to cross the voltage threshold necessary to evoke an action potential between time 0 and time 1 during the first occurrence of the biological electrical stimulus. In contrast, a resulting signal created by the addition of relatively high level electrical noise energy to the biological electrical stimulus may be too great, so that the neural axon is overwhelmed, so that the neural axon is never able to revert back to the ready state, thereby preventing an action potential from being evoked between time 2 and time 3 during the third occurrence of the biological electrical stimulus. In this case, the resulting additive signal is composed mostly of the supra-threshold electrical noise energy.

Figure 11:
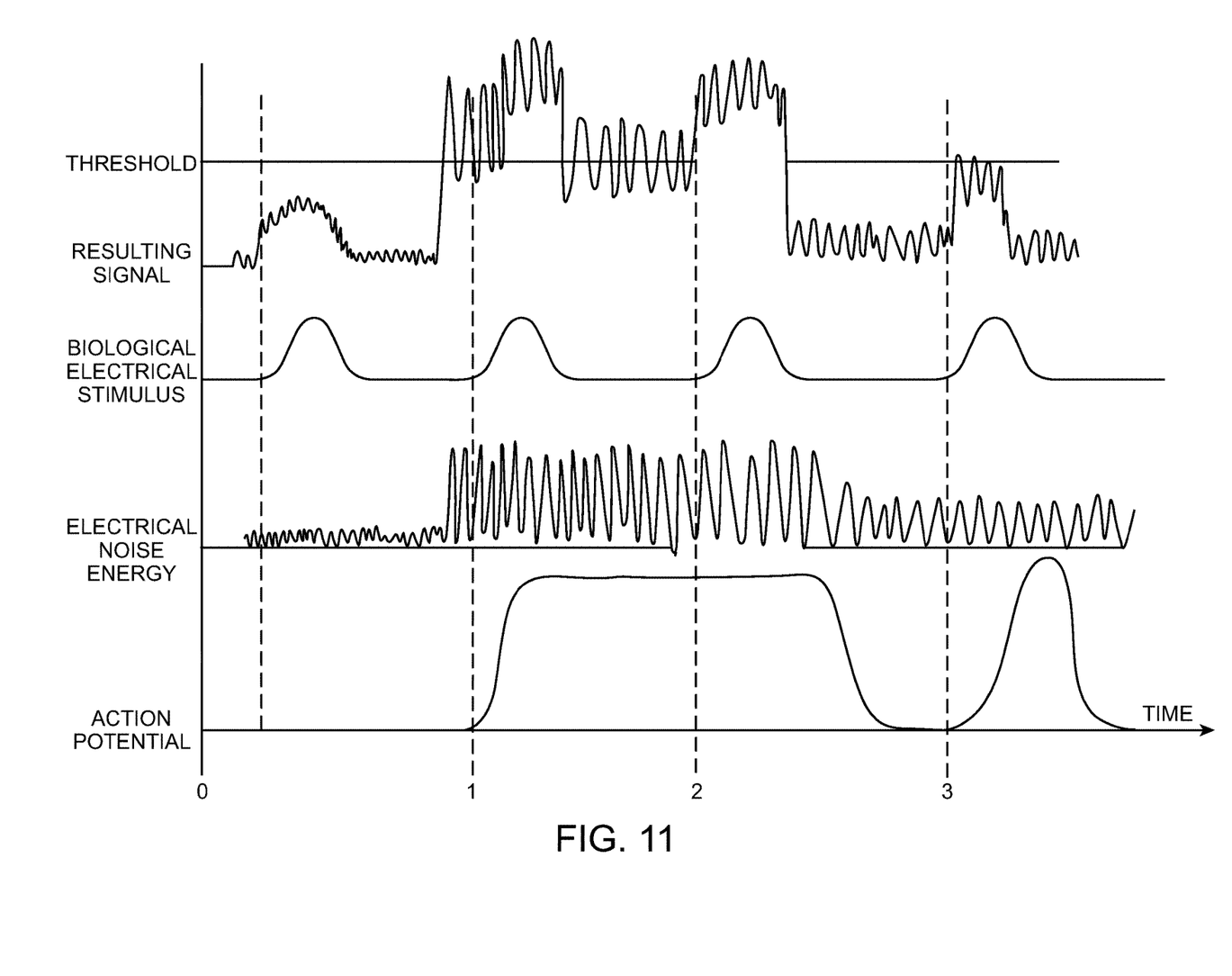
FIG. 11 is a timing diagram illustrating electrical noise energy at varying amplitude levels, a biological input signal, and a signal resulting from the integration of the electrical noise energy and biological input signal together, and the resulting action potential along a neural axon in response to the resulting signal.

However, a resulting signal created by the addition of relatively moderate level electrical noise energy to the biological electrical stimulus is just great enough to allow the action potential to be evoked between time 3 and time 4 during the fourth occurrence of the biological electrical stimulus. Thus, it should be appreciated that the magnitude of the electrical noise energy can be varied to optimize the therapy. Notably, the electrical noise energy at this moderate level is, by itself, sub-threshold, such that it will not inadvertently evoke an action potential in the absence of the biological electrical stimulus. It should also be noted, because the evoking of an action potential is an all-or-nothing phenomenon, the electrical noise energy need only add to the biological electrical stimulus in an instantaneous point in time. Thus, the signal resulting from the addition of the electrical noise energy and the naturally occurring electrical stimulus may not be continuously supra-threshold in order to evoke the action potential, but need only be supra-threshold for only the time needed to initially evoke the action potential.

Thus, it can be appreciated from the foregoing that the application of the electrical noise energy effectively increases the magnitude of the biological input signal, such that it may reach the threshold needed to depolarize the affected neuron and allow propagation of the action potential. Thus, the application of the electrical noise energy decreases the magnitude of the biological input signal needed to depolarize the neuron, thereby placing the neuron in a continuous "ready state." By increasing the neuron's responsiveness to biological input signals, the application of the electrical noise energy renders the otherwise undetectable biological signal detectable. Specifically, a weak biological input signal that cannot alone trigger an action potential (e.g., due to damage to the neuron) will be amplified by the electrical noise energy so that it will trigger an action potential. Furthermore, the use of electrical noise energy may decrease accommodation by a neuron that may otherwise get used to a repeated/predictable stimulation signal.

In one application, the brain may be aided in recovery from an injury (e.g., from an automobile accident), disorder (e.g., depression), or diseased (e.g., Parkinson's Disease) by initiating or supplementing neuroplasticity in a portion of the patient's nervous system, including the peripheral nerves, spinal cord, and/or brain. The electrical noise energy may be sub-threshold, which may produce better results than simply stimulating neurons with supra-threshold electrical noise energy. The sub-threshold stimulation increases the probability that action potentials will be evoked in response to ordinary causes of activation, such as trying to move a limb, physical therapy, or simply thinking about movement of a limb. This will allow the neurons in the neural network to become entrained together or "learn" to become associated with these types of activities. In contrast, if supra-threshold electrical noise energy is applied to the neurons, action potentials may continually be evoked when the ordinary causes of the activation are not present, which will likely result in improvement in function. In fact, neurons that are "overdriven" with supra-threshold electrical noise energy may deplete their neurotransmitters and effectively become silent.

In another example, sub-threshold electrical noise energy may be applied to a severed nerve that is regenerating. Thus, although it may be a long process for the nerve to regenerate, the functionality of the regenerating nerve may be maintained, as well as the cerebral neurons associated with the functionality of the severed nerve, by allowing afferent signals to continue to be sent to the brain via the regenerating nerve, so that other neurological functions do not "take over" the regenerating nerve's territory via neuroplasticity.

In still another example, when a patient loses the ability to hear, sub-threshold electrical noise energy may be applied to an auditory nerve, cochlea, or corresponding cerebral neurons (e.g., deep brain stimulation) to prevent neuroplasticity in the auditory sectors of the brain that may otherwise "erase" the patient's ability to hear. Thus, the application of sub-threshold electrical noise energy in this manner may increase the time window that a patient may receive an auditory device, such as a cochlear implant, after hearing loss.

In some cases, it may be desirable to apply supra-threshold electrical noise energy to neurons. For example, the supra-threshold electrical noise energy may be applied to areas of the brain to prevent or reduce neuroplasticity that may otherwise occur in those areas of the brain. Application of this electrical noise energy with such a high amplitude may cause the neurons to be confused and interrupt cyclical patterns that may cause neuroplasticity. The electrical noise energy may be applied in bursts so that the effect will be long lasting, or last long enough to end or reduce neuroplasticity. In some cases, if the application of the supra-threshold electrical noise energy adversely effects essential activities, it may be desirable to sense physiological signals associated with these essential activities, and only apply the electrical noise energy to the neurons during non-essential activity.

As another example, supra-threshold electrical noise energy can be applied to interrupt regular neuron firing patterns in the brain, e.g., to interrupt firing patterns in brain structures associated with addiction, tremor, or seizures. The addition of the electrical noise energy to regularly firing neurons may randomly change the states of gates within the neurons, such that regular firing is temporarily hindered.

As still another example, supra-threshold electrical noise energy may be periodically applied to neurons to prevent, reduce, or reverse any neurological accommodation effects that stimulation therapy (e.g., spinal cord stimulation) has had on the neurons. In this case, the electrical noise energy and the stimulation therapy are applied to the neurons at different times, so that the electrical noise energy does not affect the application of the stimulation therapy.

It should be appreciated that, while electrical noise energy has been described as being applied to the neural axon in order to provide the desired effect in combination with a biological signal or biological signals, the electrical noise energy may be applied to other parts of a neuron, including the soma of the neuron, if such application would provide the desired effect in combination with the biological signal(s).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient, the patient having a neuron to which a sub-threshold biological electrical stimulus is applied, comprising:
    applying electrical noise energy to the neuron, wherein resonance between the biological electrical stimulus and the electrical noise energy is created, such that an action potential is propagated along the axon of the neuron, wherein the neuron is an auditory nerve.

2. A method of providing therapy to a patient, the patient having a neuron to which a sub-threshold biological electrical stimulus is applied, comprising:
    applying electrical noise energy to the neuron, wherein resonance between the biological electrical stimulus and the electrical noise energy is created, such that an action potential is propagated along the axon of the neuron, wherein the electrical noise energy is a continuous signal.

* * * * *